United States Patent [19]

Barton

[11] 3,998,229
[45] Dec. 21, 1976

[54] SURGICAL MARGIN BLADE

[76] Inventor: Richard T. Barton, 658 Nimes Road, Los Angeles, Calif. 90024

[22] Filed: July 22, 1975

[21] Appl. No.: 597,996

Related U.S. Application Data

[63] Continuation-in-part of Ser. No. 524,066, Nov. 15, 1974, abandoned.

[52] U.S. Cl. .................................. 128/305; 30/121
[51] Int. Cl.² ....................................... A61B 17/32
[58] Field of Search ..................... 30/121; 128/305

[56] References Cited

UNITED STATES PATENTS

| 761,367 | 5/1904 | Fish | 30/121 |
|---|---|---|---|
| 832,944 | 10/1906 | Wicks | 128/305 |
| 1,489,603 | 4/1924 | Kracht | 128/305 UX |
| 3,683,892 | 8/1972 | Harris | 128/305 X |

FOREIGN PATENTS OR APPLICATIONS

| 1,182,547 | 1/1959 | France | 128/305 |
| 923,280 | 4/1963 | United Kingdom | 128/305 |

Primary Examiner—Channing L. Pace
Attorney, Agent, or Firm—Hamer H. Jamieson

[57] ABSTRACT

A double cutting blade with a center vertical blade, which slices a margin of tissue around the surgical site. This blade permits thereby the positive establishment of tumor or diseased tissue limits by delineating the margin of normal tissue that is free of tumor or diseased tissue.

The vertical blade of the margin blade cuts a strip of skin or tissue out to form a trench of a width the same as the width between the knives wherever the margin blade, sometimes called a trenching blade, travels so that the resultant trench conforms exactly to the normal tissue surrounding the diseased tissue or tumor, thereby saving as much normal tissue as possible.

6 Claims, 8 Drawing Figures

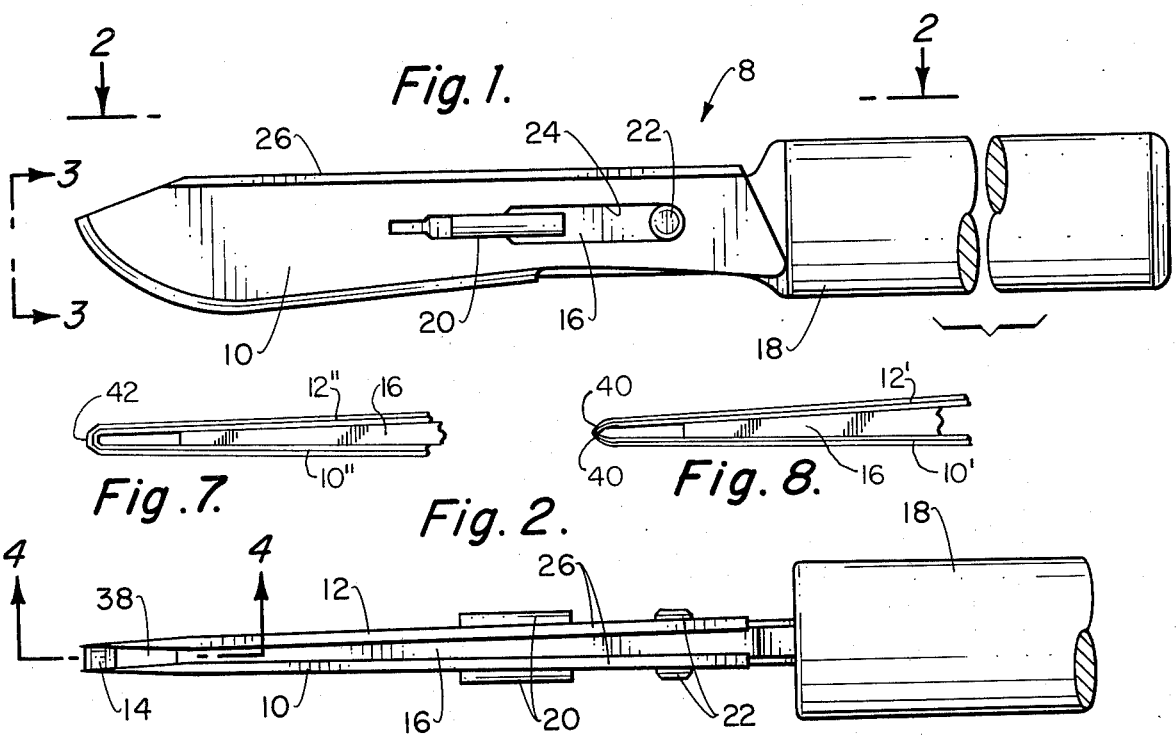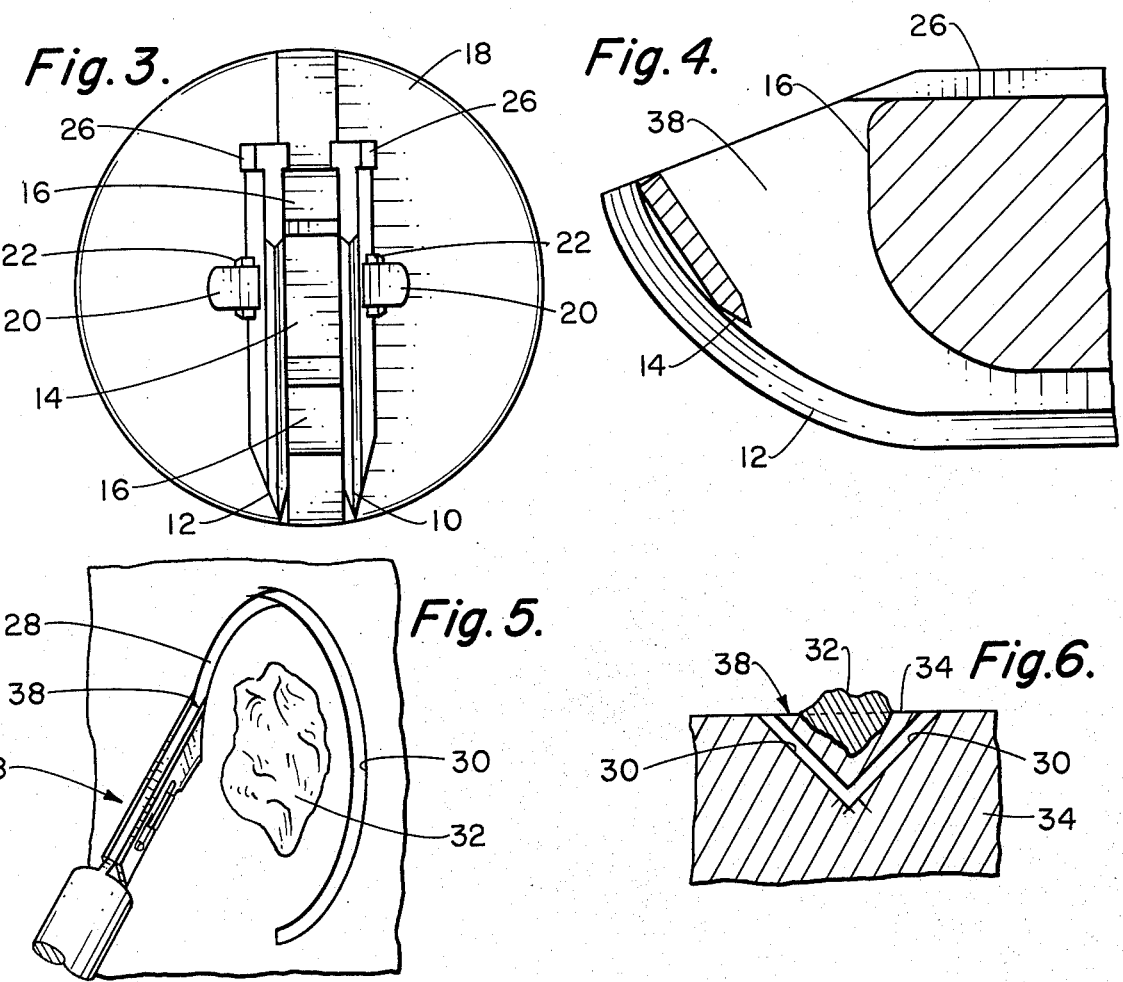

SURGICAL MARGIN BLADE

This is a continuation-in-part of my application Serial No. 524,066, filed Nov. 15, 1974, and now abandoned.

SUMMARY OF THE INVENTION

The preferred embodiment of the invention is a blade-holding device with an integrally connected handle for gripping by the fingers of a hand in the same manner as where a single handle on a single blade is held in the hand for slicing, having removably mounted slicing blades. There is a right and a left blade mounted in parallel registering silhouette on either side of the blade-holding device a predetermined desired distance apart, that distance being the same as the desired width of the trench to be cut. In one embodiment there is a third or center blade mounted between the other two blades so as to cut or slice and remove the trench between the cuts made by the two (right and left) other blades, thereby exactly outlining the diseased tissue or tumor area within the resultant trench which is to be surgically removed after the trenching operation is completed, leaving thereby the most possible normal, healthy tissue. In another embodiment the third blade is omitted and the other two blades are configured to perform its function.

An essential feature of the invention is the provision of a double cutting blade or two parallel cutting portions mounted a fixed, predetermined width or space apart with a center blade portion between them which slices a margin of tissue around the surgical site. It may be used to positively establish tumor limits by delineating the margin of tissue that is free of tumor.

Secondary uses are in biopsing tumor masses, lympth nodes, and other organs with a minimum of tissue disturbance. It is also of value in plastic surgery, wherein cartilage is serially sliced to contour.

A typical use of the invention is in the excision of skin tumors where the limit of the tumor is not clearly identified.

The blade is made in a variety of sizes and shapes, and the nature of the tumor and its location determine which particular size and shape blade is best suited for the procedure. The blade is pressed into the tissue in a manner similar to that used with any other surgical blade; and as the tip enters, the blades cut a thin slice of preferably 2 millimeters (depending on the width of the particular blade being used).

The margin around the tumor is usually cut in an ellipse, which yields two slices that are then examined for evidence of tumor by a pathologist in a frozen-section technique.

BRIEF DESCRIPTION OF THE DRAWINGS

Other objects, uses, and advantages will be made to appear in the following description and drawings, wherein:

FIG. 1 is a side view of a preferred form of the invention;

FIG. 2 is a view taken along line 2—2 of FIG. 1;

FIG. 3 is a view taken along line 3—3 of FIG. 1;

FIG. 4 is a view taken along line 4—4 of FIG. 2;

FIG. 5 shows cutting a circular path around cancer;

FIG. 6 is a cross-sectional view of cancer about to be removed; and

FIGS. 7 and 8 illustrate modified forms of the invention.

DESCRIPTION OF THE PREFERRED EMBODIMENT

Turning now to the details shown in FIGS. 1 to 6 of the drawings, the knife assembly 8 includes a right blade 10, a left blade 12, and a center blade 14, the right and left blades being removably mounted on a blade-holding device 16, which is removably connected to an ordinary handle 18. Handle 18 is used for gripping by the user's fingers and hand in the same way that a handle having a single blade is held in the user's hand for slicing.

A protrusion section 20 on the blade-holding device 16 is provided identically on both sides of the blade-holding device. Each protrusion 20 is received by a slot 24 in its respective blade (right blade 10 or left blade 12, as the case may be). A suitable blade stop 22 is provided on each side of blade-holding device 16 for removably mounting blades 10 and 12. Other suitable means for removably mounting said blades 10 and 12 on protrusions 20 may be alternatively supplied. In this way, fresh blades can easily and quickly be exchanged for used blades whenever desired. A center blade 14, fixed to the tips of the blades 10 and 12 extends between them with its cutting edge extending in the same direction.

As the two cutting blades 10 and 12 are inserted into the skin to cut and slice it at the angle preferably shown in FIG. 5, the cutting edge of the center blade 14 cuts the tissue leaving a trench as wide as the fixed, lateral distance between the two slicing blades 10 and 12 and as deep as the center blade 14 is is permitted to enter by its fixed mounting between slicing blades 10 and 12. In this way, a strip of skin 28 and tissue attached thereto is removed, leaving a cavity or trench 30 (see also FIG. 6) which sharply delineates the area to be removed in order to completely remove the tumor or cancer between the outside edges of the surrounding trench or cavity 30.

In this way, the cancer 32 is completely removed. Also, the skin 36 adjacent the cancer and inside the surrounding cavity 30 is also removed, thereby leaving a clean, cancer-free area within the surrounding walls formed by the cut made by the outside blade, 10 or 12, as the case may be, as well as leaving walls of healthy tissue surrounding the area. This is of great value in making extremely accurate delineation of the cancerous material to be removed so as to save as much normal, healthy tissue and skin as possible.

A slot or feed-through 38 is provided adjacent center blade 14 (See FIG. 5) to permit the removal and efficient disposal of the cut-away skin and tissue removed by the trench knife to form the trench surrounding the tumor or cancer.

FIGS. 7 and 8 show alternative forms of the surgical knives in a fragmentary manner, showing only the tips of the knives and a portion of their support element 16. It is contemplated that in these forms of the invention the blade or blades may be secured to a suitable handle in the manner already described.

In FIG. 7 the blade, instead of being two separate elements joined by a third transverse blade, is formed of generally U-shape having one blade portion 10 inches and integral blade portion 12 inches joined by a bight portion 42. Thus the integral blade structure provides for a cutting blade portion and a trenching blade portion in a single structure.

In FIG. 8 the separate blades 10' and 12' have their outer end portions 40 bent inwardly into substantial contact and thus the inwardly bent portions function as the transverse blade 14 of FIG. 2 or the blade portion 42 of FIG. 7.

Obviously, the modifications of FIGS. 7 and 8 may be employed in exactly the same manner as already described with reference to the previous embodiment.

Various equivalent variations may obviously be made in the above preferred embodiment without departing from the spirit and the protected elements, mode of operation, and scope of the appended claims.

What is claimed is:

1. A surgical knife comprising:
   an elongated handle having blade holding means at one end thereof;
   blade means secured to said blade holding means, said blade means having laterally spaced elongated slicing blade portions extending endwise from said handle and a transverse trenching blade portion spanning the space between said slicing blade portions adjacent the outer ends thereof and all of said blade portions having cutting edges facing the same direction lateral to the length of said handle.

2. A knife as defined in claim 1 wherein said slicing blade portions are separate blades removably secured to opposite sides of said blade holding means.

3. A knife as defined in claim 2 wherein said blade holding means is removably mounted on said handle whereby blade holding means of different widths can be mounted thereon.

4. A knife as defined in claim 1 wherein said slicing blade portions comprise separate blades and said trenching blade portion comprises an end portion of at least one of said blades bent inwardly toward the other blade.

5. A knife as defined in claim 4 wherein both said blades are provided with end portions bent toward each other.

6. A knife as defined in claim 1 wherein said blade means comprises a single elongated blade bent to generally U-shape, the spaced legs thereof defining said slicing blade portions and the bight portion of which defines said trenching blade portion.

* * * * *